United States Patent [19]
Goldschmidt et al.

[11] Patent Number: 5,880,380
[45] Date of Patent: Mar. 9, 1999

[54] HIGH CONTAINMENT SAMPLER

[76] Inventors: Norman Goldschmidt, 622 Roberts Ave., Syracuse, N.Y. 13207; Kenton Shultis, 7644 Charlemont Dr., Manlius, N.Y. 13104

[21] Appl. No.: 841,219

[22] Filed: Apr. 29, 1997

[51] Int. Cl.[6] ....................................................... G01N 1/02
[52] U.S. Cl. ............................. 73/863.85; 73/863.84; 73/864.16; 73/864.14
[58] Field of Search ............................. 73/864.14, 864.16, 73/864.17, 864.18, 864.13, 864.15, 863.86, 863.84, 863.81, 863.85

[56] References Cited

U.S. PATENT DOCUMENTS

| | | | |
|---|---|---|---|
| 3,321,977 | 5/1967 | Topham | 73/422 |
| 3,417,623 | 12/1968 | Andrasko | 73/422 |
| 3,638,499 | 2/1972 | Saint-Andre | 73/422 R |
| 3,766,785 | 10/1973 | Smernoff | 73/864.16 |
| 3,830,108 | 8/1974 | Spong | 73/864.16 |
| 3,933,048 | 1/1976 | Scordato | 73/864.17 |
| 4,458,543 | 7/1984 | Mieth | 73/863.86 |
| 4,580,452 | 4/1986 | Masson | 73/863.86 |
| 4,580,453 | 4/1986 | Taylor | 73/863.86 |
| 4,625,571 | 12/1986 | Slator | 73/863.84 |
| 4,682,507 | 7/1987 | Terrell | 73/863.57 |
| 5,129,267 | 7/1992 | Nicholls | 73/863.84 |
| 5,251,495 | 10/1993 | Kuhner | 73/863.71 |
| 5,364,596 | 11/1994 | Magnussen, Jr. et al. | 73/864.14 |
| 5,531,131 | 7/1996 | Sabloewski | 73/864.16 |

FOREIGN PATENT DOCUMENTS

| | | | |
|---|---|---|---|
| 858148 | 12/1952 | Germany | 73/864.16 |

*Primary Examiner*—Hezron Williams
*Assistant Examiner*—Nashmiya Fayyaz
*Attorney, Agent, or Firm*—Morton S. Simon

[57] ABSTRACT

There is disclosed a high containment device, apparatus or system for withdrawing sample material from process or manufacturing equipment with substantially no leakage of the sample material to the external environment and which is of syringe-type construction, thus preventing possible contamination of such environment or workers operating processing and/or production equipment in such a situation, especially where hazardous materials are involved. The high containment device, apparatus or system disclosed is used in combination with process or manufacturing equipment thus providing a system which results in the prevention of leakage of possible hazardous material to the environment and possible contamination of equipment operators thereby.

7 Claims, 2 Drawing Sheets

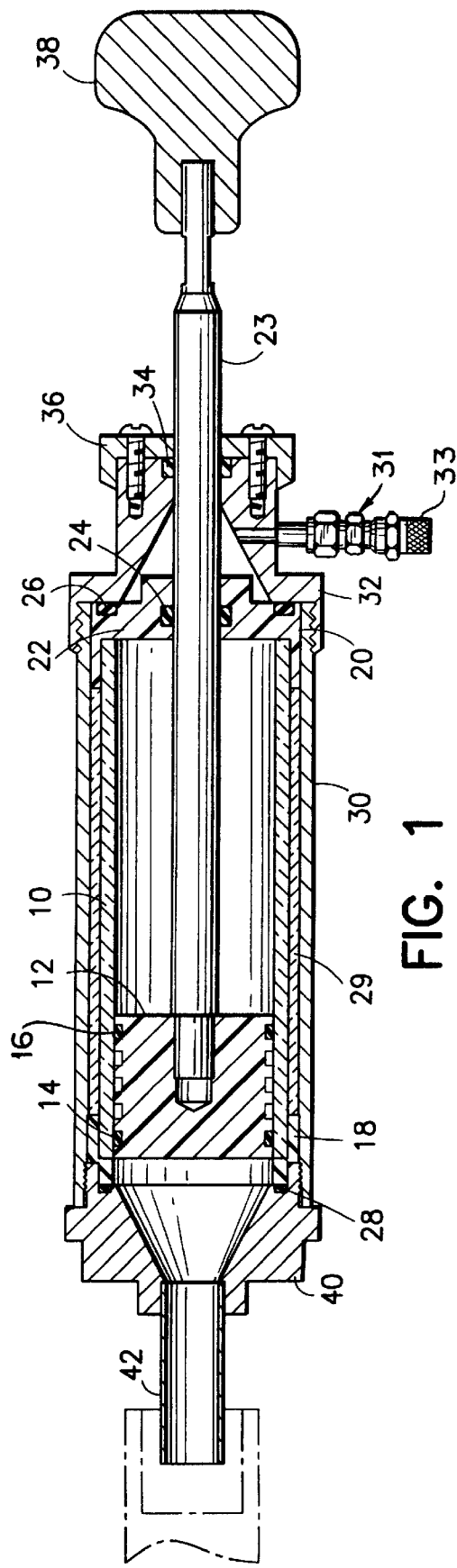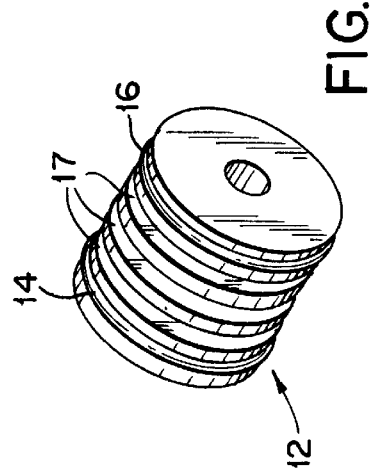
FIG. 1
FIG. 2

HIGH CONTAINMENT SAMPLER

This invention relates to a sampler, or sampling device or system. More particularly, it relates to a high containment sampler, or sampling device or system which allows samples of hazardous materials to be taken from a pipe or line which is part of manufacturing and/or processing equipment utilized in making or processing hazardous materials and which permits samples of such materials to be taken from the system without compromising the purity or endangering operators of the equipment, as well as the environment.

BACKGROUND OF THE INVENTION

A wide variety of sampling devices or systems which permit the withdrawal of samples from a production or processing equipment line are known. Moreover, dependent upon the materials being made or processed, that is, whether they are hazardous materials or innocuous materials, various devices have been developed for withdrawing samples from a pipe, which is part of the production line, or from other elements of a production line. Moreover, such sampling systems, devices or equipment vary greatly with respect to their complexity, as well as their particular construction, in order to prevent any leakage to the external environment which results not only in loss of materials and the need for moping up operations, as well as preventing contamination of process or manufacturing operators and the external environment.

Examples of such systems, devices and the like include U.S. Pat. No. , 3,321,977 issued May 30, 1967, to Topham. It discloses a sample injection valve having a chamber with an inlet port and an outlet port, as well as a port to permit material to be expelled from a chamber. Another example of a fluid sampler is disclosed in U.S. Pat. No. 3,417,623 issued Dec. 24, 1968 to Andrasko. It discloses a sampler for removing a fluid sample from a closed conduit. It employs a tubular bushing that is permanently installed transverse to the conduit. Another example of a sampler is U.S. Pat. No. 3,638,499 issued Feb. 1, 1972, to Saint-Andre, discloses a device for taking samples of fluid from a hydraulic circuit while operating under pressure. The device comprises a hollow body having a chamber connected into the circuit through a very small opening that is normally closed by a point at the end of a spring-pressed plunger slidable in the chamber and having near the point lateral channels which lead into a central longitudinal channel through which the sample is discharged when the plunger is pulled down against its spring in order to open the opening. This device also includes a controlled-leakage passage which prevents accumulation of solid particles, thus keeping the device clean and preventing contamination of subsequent samples.

Still further, U.S. Pat. No. 4,458,543 issued Jul. 10, 1984 to Mieth, discloses a cleanable sampling valve which may be incorporated into the product line of a manufacturing equipment arrangement. Additionally, U.S. Pat. No. 4,580,452 issued Apr. 8, 1986 to Masson discloses a device for taking a liquid from a conduit which contains the liquid or for injecting a liquid into the conduit. Patentee discloses a valve mounted on a conduit from which a sample of liquid which flows along the conduit may be withdrawn or material may be injected into the conduit. Still further, U.S. Pat. No. 4,580,453 issued Apr. 8, 1986 to Taylor, discloses a gear case oil sampling device for use with a gear case which contains a quantity of lubricating oil. An axially bored access plug is connected to the gear case. The plug includes an oil tube immersed in the lubricating oil when the gear system is idle. An air core valve normally closes the plug bore. In this device, an oil sample container is disposed slidably around a piston for longitudinal movement of the container relative to the piston and an axially bored piston rod projects out of the container open end and is connectable with the access plug in a plug valve opening manner to provide fluid communication between the container and the gear case oil. Still further, U.S. Pat. No. 4,625,571 issued Dec. 2, 1986 to Slater, discloses a grab sampler for liquids and especially for crude oil flowing through pipelines. The sampler is provided with a set of concentric tubular members including an outer body, an inlet and outlet; and a sleeve and hollow piston, respectively axially slideable within the body and sleeve. The piston is provided with an internal and non-return valve at its base. The sleeve, piston base and body are capable of defining a sample chamber so as to trap a sample of liquid flowing through the pipeline. Application of pressure on the piston displaces the trapped sample through the non-return valve to the inside of the piston and is recovered therefrom by sample removal means.

Still further, U.S. Pat. No. 4,682,507 issued Jul. 28, 1987 to Terrell, discloses an apparatus for removing a sample from a material conveying conduit and delivering the sample to a remote testing or other deposit location without any manual handling of the sample. Additionally, U.S. Pat. No. , 5,129,267 issued Jul. 14, 1992 to Nicholls, discloses an on-line product sampling apparatus for measuring product samples from a product stream in a flow line having a sampling aperture. The apparatus includes a sampling tube which contains product samples that a piston removes from the flow line via the aperture. The piston cycles through a sample-return cycle, during which it removes a product sample from the product stream and then returns it to the product stream. The sampler is provided with a sensor for sensing physical properties of the removed product samples during the time they are held within the sample tube and during the piston cycle.

Finally, U.S. Pat. No. 5,251,495 issued Oct. 12, 1993 to Kuhner, discloses a closed loop sampling system using quick-connects. The system dramatically reduces emission of sampled hydrocarbons and other fluids to the external atmosphere.

As is readily apparent from the various Patents mentioned above, sampling devices and the like, such as those described in these Patents, are relatively complex in structure and, while they generally achieve the objects for which they were developed, in a satisfactory manner, there still exists a need for sampling devices and systems which are simple in structure, while still acting in a manner to provide high containment of any materials being removed from a production line for purposes of sampling the same and preventing any substantial leakage or the like of any hazardous materials to the surrounding environment and thus preventing contamination of the environment, and operators of the production line. The present invention fulfills such needs.

BRIEF STATEMENT OF THE INVENTION

Thus, according to the inventive concept of this case, there is provided a high containment device for withdrawing sample material from process or manufacturing equipment with substantially no leakage of sample material to the external environment. The device has a syringe-type construction and comprises a barrel, piston means located and reciprocally movable in the barrel, sealing means located at opposite ends of the barrel, at least one of the sealing means at one end of the barrel being supported in a holder means provided with a central opening, a plunger shaft passing through the opening and anchored at one end in the piston means and provided at its opposite end with handle means for reciprocating the piston means in the barrel and a holder means including quick connect-disconnect means located at the end of the barrel opposite the handle means opening into the barrel at one end and provided with male quick connect-disconnect means at its opposite end for cooperative connection with quick connect-disconnect female means located in a pipe of processing or production equipment for withdrawing a sample from such equipment and upon withdrawing of the piston means through the barrel introducing the sample into the barrel with substantially no leakage of the sample to the external environment.

Still further, the high containment device of this invention includes an outer sleeve disposed around the barrel and a first end cap disposed over one end of the sleeve and a second end cap disposed over the opposite end of the sleeve. The first end cap is located in the vicinity of the handle means and is provided with a central opening for passage of the plunger shaft therethrough and into the interior of the barrel and the opposite second end cap encloses the opening in the other end of the barrel and is provided with an opening in which the quick connect-disconnect means provided with the male quick connect-disconnect means is disposed.

Still further, in accordance with the invention, there is provided a high containment sampling system, device or apparatus which allows samples of hazardous materials to be taken without compromising the purity, endangering workers operating the system or introducing hazardous materials into the environment. The inventive system, device, or apparatus of this invention comprises a syringe construction including a standard captured glass pipe type sight glass barrel provided with a piston having multiple O-ring seals and provided with intermediate channels to allow the trapping of leaked material and thus the detection of a leak, and, at the same time, minimizing carry-through from a single seal leak. A plunger rod or driving shaft provided with a shaft seal and a handle, such as a "Tee" handle, is connected to the piston for purposes of reciprocating the piston within the sight glass pipe or barrel allowing visual inspection of the sample and providing vacuum as may be needed for sampling. The tip of the syringe thus form a double ended shut-off disconnect. The pipe, in the production line equipment to be sampled, is connected with a throttling valve and the female end of a quick disconnect. The size of the sight glass may vary widely, but generally is made to receive a 100 cc sample from a pipe or vessel in a widely varying pressure range which may extend from about 80 psi to a significant vacuum with no more than 0.1 cc leakage at each end. The unit can be disassembled completely for cleaning and the various materials employed are also autoclavable. The sight glass or glass barrel is preferably located within an outer sleeve which may be made of stainless steel or the like. The glass barrel is also preferably surrounded by a captured plastic sleeve for safety and containment.

THE DRAWINGS

In order to understand the present invention more fully, reference is directed to the accompanying Drawings which are to be taken in conjunction with the following detailed description of the preferred embodiments of the system, device or apparatus of the invention and wherein:

FIG. 1 illustrates the high containment sampling system, device or apparatus of the invention and is a diagrammatic view in section of the inventive system, device or apparatus;

FIG. 2 is a partial view in perspective of the piston means illustrated in FIG. 1 removed from the system, device or apparatus of this invention showing the channels provided in the piston body and the two channels near the ends of the piston having O-ring seals disposed therein; and FIG. 3 is a plan view of a device or apparatus partially in section, according to the invention, showing the outer sleeve made of stainless steel and the open structure thereof which permits viewing of the piston and detail thereof through the open areas of the outer sleeve and through the partially shown plastic sleeve which surrounds the partially shown pipe glass barrel.

DESCRIPTION OF THE PREFERRED EMBODIMENTS

Figure 3:
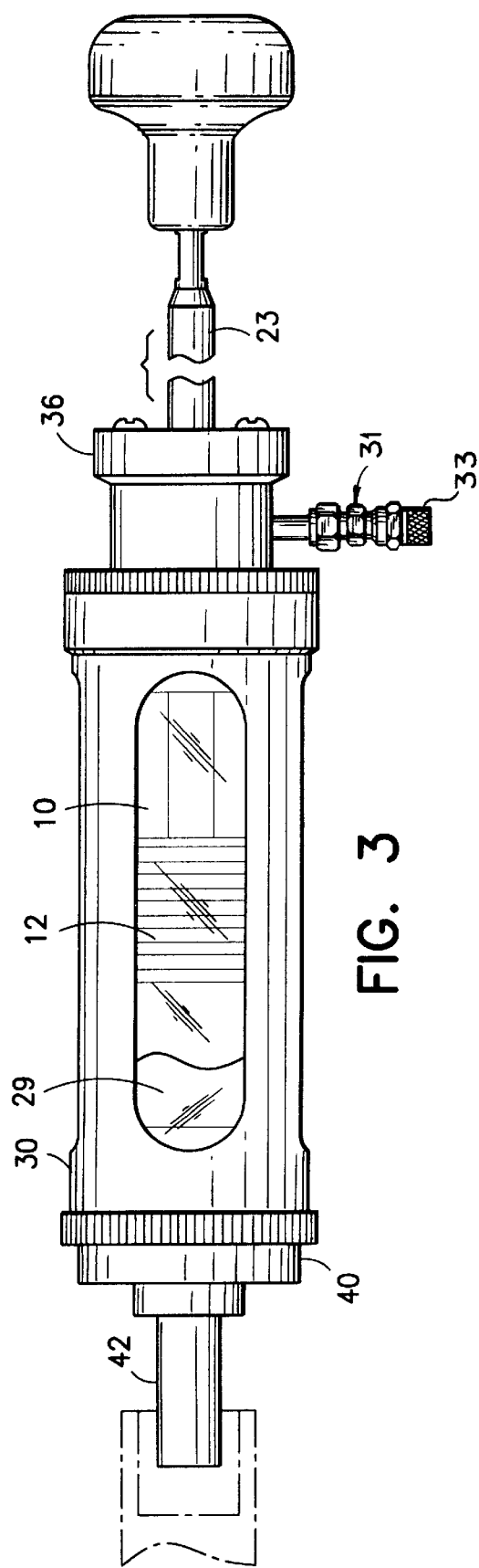

Referring now more particularly to the accompanying Drawings, the system, device or apparatus according to the invention illustrated in FIG. 1, comprises a syringe-type construction provided with a glass barrel 10 which is made of a captured glass pipe type of sight glass having disposed therein a plunger or piston 12 capable of being reciprocated longitudinally within the barrel 10. The plunger or piston 12 is provided, as shown in FIG. 2, with a plurality of O-ring seals 14 and 16, for example, located near each end of piston 12 and with intermediate channels 17. Such an arrangement assures against leakage around the piston 12 to other areas of the barrel 10 and it is to be understood that additional O-ring seals can be provided in the channels 17, if desired. The plunger or piston is preferably made of teflon or other suitable materials, while the O-ring seals disposed around the plunger are preferably made from silicon or the like and encapsulated within teflon in order to provide facility of movement of the piston within the barrel while at the same time ensuring prevention of leakage but allowing rather facile reciprocation of the plunger or piston within the barrel.

It is to be understood that it is within the purview of this invention that the plunger or piston 12, as well as the seals disposed around the same, may be made of any other suitable materials so long as they permit not only good sealing, but relatively free movement of the piston within the barrel.

At one extremity of barrel 10, a seal 18, preferably of teflon, is provided. At the opposite end of barrel 10, there is provided a seal 20, preferably of teflon, and an O-ring holder 22. Holder 22 is provided with a central opening for passage of a plunger shaft 23 and has a central opening in which an O-ring seal 24, preferably of teflon encapsulating silicon, is located. Plunger shaft 23 passes through a central opening in the O-ring seal 24 which also forms a shaft guide for the plunger shaft 23 and is anchored in the plunger or piston 12. Another O-ring seal 26 is located on the external surface of the O-ring holder 22. A still further O-ring seal 28 is located at the opposite end of barrel 10. The barrel 10 is surrounded by a captured plastic sleeve 29 which acts as a safety shield in the event the barrel should fail. The sleeve 29 may be made of any strong, clear, inert plastic, such as, for example, polyvinyl chloride plastics, polyamide plastics, polypropylene plastics, polyethylene plastics and the like.

The described elements of a system, device or apparatus, according to the invention are preferably further enclosed within an outer sleeve 30, preferably of stainless steel, and which has an open or windowed construction, as shown in FIG. 3. Sleeve 30 is further provided at one end with an end cap 32, preferably of stainless steel. End cap 32 is provided with a central opening for passage of the plunger shaft 23 and, as well, with a spring loaded shaft seal 34 to ensure substantially complete sealing of the shaft within the end cap. End cap 32 is also provided with a shaft seal retainer 36 which is also provided with a central opening for passage of the plunger shaft 23. The plunger shaft 23 is further provided with a handle 38, preferably a "T" handle, for purposes of reciprocating the plunger shaft and thus the piston in the glass barrel 10.

The system, device or apparatus of this invention is also preferably provided with a relief means, such as sealable breather or relief valve 31, which can be set in employed and unemployed positions. More specifically, in the event of a leak around the piston 12 when a sample is taken, valve 31 can be activated by rotating the knurled knob 33 to an employed position, thus permitting any pressure build-up to be relieved by allowing flow of sample which has leaked past the piston and into the barrel to be introduced into the interior of the sealable breather or relief valve 31. Alternatively, valve 31 can be employed to allow an inert gas, such as nitrogen or argon, or sterile air, or even an inert liquid, such as mineral oil, or process solvent to be introduced into and fill the seal space behind the piston. Thus, as the piston moves, or is moved back to bring in a sample, the gas or fluid barrier behind the piston can be exhausted through valve 31, and/or returned to a fluid reservoir (not shown) adapted to be cooperatively used with valve 31. Consequently, valve 31 not only provides safety advantages, but also provides protection to the sample being withdrawn from the process, as well as to the process per se, from adventitious oxygen, moisture or microbes and other possible contaminants and the like. Suitable sealable breather or relief valves, such as 31, are known in the industrial processing field and readily available through commercial channels.

At the opposite end of the device, an additional end cap 40, preferably of stainless steel, is provided to completely seal the glass barrel, and its related elements, within outer sleeve 30. End cap 40 is provided with a quick connect-disconnect element 42 (shown diagrammatically) which is provided with a male connecting system, as is well known in the art. This male quick connect-disconnect apparatus cooperates with a quick connect-disconnect female element located in the pipe of a processing or manufacturing system in the manner known in the art. This female quick connect-disconnect element is not shown.

It is to be understood, however, that any suitable quick connect-disconnect devices, such as those known in the art and manufactured by Swagelok Quick-Connect Co. of Hudson, Ohio, may be employed when utilizing the sampling system, device or apparatus of this invention.

In use, the system, device or apparatus of the invention, operates generally as follows. The above-described quick connect-disconnect devices are connected to each other and the plunger is utilized to move the piston away from one end of the device by withdrawing the plunger shaft and moving the piston toward the opposite extremity of the glass barrel, thus, withdrawing a sample from the pipe of the processing or producing equipment. When the sample is withdrawn, the quick connect-disconnect male and female members are disconnected from each other and the sample is substantially completely sealed within the barrel of the device which may then be moved to another location for opening the male quick connect-disconnect element 42 in the manner known in the art and thus permitting the sample to be withdrawn from the glass barrel or injected into another sealed apparatus, for example, for testing of the sample, as needed.

When the testing has been concluded, the sealed device containing the material used for testing is simply discarded without any substantial leakage of the sample material from either the testing device or the system of this invention. Sampling may be repeated as often as needed and the samples taken can likewise be injected into a testing apparatus or into further containers which are provided with quick connect-disconnect devices, such as those briefly referred to above, without the danger of any contamination to workers or the external atmosphere. Thus, the device ensures substantially complete protection against leakage and contamination of exterior areas.

The system, device or apparatus of this invention presents many advantages. It provides an ultra low leakage system, device or apparatus which is relatively simple in construction. Moreover, it employs elements which are readily available through commercial channels and which are made of materials which are readily available commercially and which allow for complete disassembly of the device and cleaning, as well as autoclaving, of the elements, as needed, for further reuse.

Furthermore, while the various elements of the device are made of, preferably, teflon and silicon encapsulated teflon, other like materials may be utilized in place thereof so long as they present the degree of substantially leak-free sealing and operation.

In addition, since the elements of the device are relatively useful over substantial periods of time, those elements which need replacement can be obtained easily on the open market, replacement parts, as needed, can be obtained readily while retaining the old elements for further use.

Still further, while the device is generally made to take samples, preferably of a capacity of about 100 cc's, the device may be made in a wide variety of sizes depending upon the particular amount of sample needed to carry out one or a plurality of tests.

Numerous other advantages of the invention will be readily apparent to those skilled in the art.

It is to be understood that various modifications of the system, device or apparatus of this invention may be made without departing from the spirit and scope of the invention. It should be further understood that this invention is not to be limited to the embodiments described herein, except as defined in the appended claims.

What is claimed is:

1. A high containment device for withdrawing sample material from process or manufacturing equipment with substantially no leakage of said sample material to the external environment, said device having the construction of a syringe and comprising a barrel, piston means located and reciprocally movable in said barrel, sealing means located at opposing ends of said barrel, at least one of said sealing means at one end of said barrel being supported in a holder means provided with a central opening, a plunger shaft passing through said opening and anchored at one end in said piston means and provided at an opposite end of said shaft with handle means for reciprocating said piston means in said barrel, second holder means including quick connect-disconnect means located at the end of said barrel opposite said handle means and said second holder means opens into said barrel and is provided with male quick connect-disconnect means for cooperative connection with quick connect-disconnect female means located in a pipe of processing or manufacturing equipment for withdrawing sample material from said equipment and upon withdrawing of said piston means through said barrel introducing said sample material into said barrel with substantially no leakage of said sample material to the external environment.

2. The high containment device as defined in claim 1, including an outer sleeve disposed around the barrel and having a first end cap disposed over and enclosing one end of said sleeve and a second end cap disposed over and enclosing an opposite end of said sleeve, the first end cap being located in the vicinity of the handle means and provided with a central opening for passage of the plunger shaft therethrough and into the interior of said barrel and the second end cap being disposed over the opposite end of said sleeve and enclosing an opening in the opposite end of said barrel and being provided with an opening in which the male quick connect-disconnect means is disposed for cooperation with the female quick connect-disconnect means located in the pipe of the processing or manufacturing equipment.

3. The high containment device as defined in claim 2, including a captured plastic sleeve disposed around the barrel and located inside the outer sleeve.

4. The high containment device as defined in claim 2, wherein the outer sleeve is made of stainless steel.

5. A high containment device for withdrawing sample material from process or manufacturing equipment with substantially no leakage of said sample material to the external environment, said device having the construction of a syringe and comprising in combination a barrel, piston means located and reciprocally movable in said barrel, sealing means located at opposing ends of said barrel, at least one of said sealing means at one end of said barrel being supported in a holder means provided with a central opening, a plunger shaft passing through said opening and anchored at one end in said piston means and provided at an opposite end of the shaft with handle means for reciprocating said piston means in said barrel, second holder means including quick connect-disconnect means located at the end of said barrel opposite said handle means and said second holder means opens into said barrel and is provided with male quick connect-disconnect means for cooperative connection with quick connect-disconnect female means located in a pipe of processing or manufacturing equipment for withdrawing sample material from said equipment and upon withdrawing of said piston means through said barrel introducing said sample material into said barrel with substantially no leakage of said sample material to the external environment; an outer sleeve disposed around said barrel; said outer sleeve having a first end cap disposed over and enclosing one end of said sleeve and a second end cap disposed over and enclosing an opposite end of said sleeve, the first end cap being located in the vicinity of the handle means and provided with a central opening for passage of the plunger shaft therethrough and into the interior of said barrel and the second end cap being provided with an opening in which the male quick connect-disconnect means is disposed for cooperation with the processing or manufacturing equipment.

6. The high containment device as defined in claim 5, including a captured plastic sleeve disposed around the barrel and located inside the outer sleeve.

7. The high containment device as defined in claim 5, wherein the outer sleeve is made of stainless steel.

\* \* \* \* \*